United States Patent
Markart

(10) Patent No.: US 7,327,451 B2
(45) Date of Patent: Feb. 5, 2008

(54) TEST STRIP SYSTEM

(75) Inventor: Ernst Markart, Munich (DE)

(73) Assignee: LRE Technology Partner GmbH, Munich (DE)

( * ) Notice: Subject to any disclaimer, the term of this patent is extended or adjusted under 35 U.S.C. 154(b) by 785 days.

(21) Appl. No.: 10/043,681

(22) Filed: Jan. 10, 2002

(65) Prior Publication Data
US 2002/0114735 A1 Aug. 22, 2002

Related U.S. Application Data
(62) Division of application No. 09/218,327, filed on Dec. 22, 1998, now abandoned.

(30) Foreign Application Priority Data
May 20, 1998 (DE) ................. 198 22 770

(51) Int. Cl.
G01N 21/01 (2006.01)
G01N 31/22 (2006.01)

(52) U.S. Cl. .................. 356/244; 422/82.05; 422/58; 422/61; 422/68.1

(58) Field of Classification Search ............... 422/58, 422/61, 82.01, 68.1, 82.05; 356/244
See application file for complete search history.

(56) References Cited

U.S. PATENT DOCUMENTS 4,780,283 A * 10/1988 Meinecke et al. ....... 422/82.05
4,934,817 A * 6/1990 Gassenhuber ............... 356/446
5,091,154 A 2/1992 Pauli et al. .................... 422/63
5,281,395 A * 1/1994 Markart et al. .......... 422/82.05
5,424,035 A * 6/1995 Hones et al. .................. 422/55
5,597,532 A 1/1997 Connolly ..................... 422/58

FOREIGN PATENT DOCUMENTS

DE 77 25 947 U1 12/1977
EP 0 319 922 6/1989
EP 0 333 099 A2 9/1989

\* cited by examiner

Primary Examiner—Jill Warden
Assistant Examiner—Paul S Hyun
(74) Attorney, Agent, or Firm—McCormick, Paulding & Huber LLP

(57) ABSTRACT

The present invention provides a test field system, including a test strip with a test field, and a measuring device having a test strip receiver for measuring the test field. The test strip receiver inducing a support surface for the test strip and positioners for holding the test strip inserted in the strip receiver so that a section of the test strip containing the test field is held in a definite position relative to the support surface. The strip receiver having two holding members spaced from one another on edge areas of the support surface for holding fast associated edges of the test strip substantially adjacent the support surface, the support surface in a middle area between the holding means is vertically displaced from the edge areas such that the test field of a test strip inserted in the test strip receiver is spaced apart from the support surface.

3 Claims, 4 Drawing Sheets

TEST STRIP SYSTEM

CROSS REFERENCE TO RELATED APPLICATIONS

This application is a divisional application of U.S. patent application 09/218,327 filed on Dec. 22, 1998, and abandoned on Jan. 11, 2002.

FIELD OF THE INVENTION

The invention concerns a test strip system including at least one test strip with a test field; and for measuring the test field, a measuring device with a strip receiver having a support surface for the test strip, and positioning means, by means of which the inserted test strip is so held in the strip receiver that at least the test field containing section of the test strip takes on a definite position relative to the support surface.

BACKGROUND OF THE INVENTION

A test strip system of the above-mentioned kind is known, for example, from U.S. Pat. No. 5,424,035. In the solution there described, the support surface rises slightly at the inner end of the strip receiver and has a pin intended to be received in a recess of the strip. Between this holding pin and the spot at which the test field of the test strip is to come to lie in the strip receiver is a rigid pressing element opposite the support surface, the spacing of which pressing element from the support surface is slightly more than the thickness of a test strip. By means of this arrangement the test strip is pressed in slightly bent condition against the support surface so that the test strip, on one hand, hangs firmly on the pin and; on the other hand, the test field, by the bending of the test strip, is pressed against the support surface. The insertion and especially the removal of the test strip are each difficult and complicated and the danger exists that the user, in attempting to pull the test strip from measuring device, either dirties the device or his fingers.

The invention has as its object the provision of a test strip system of the a foregoing kind in which the test strip, especially the test field, is held in a definite position with the insertion and removal of the test strip into and out of the strip receiver being simple and easy.

SUMMARY OF THE INVENTION

This object is solved in accordance with the invention in that the test strip is pressable against an abutment of the strip receiver by a spring force working parallel to the support surface. The abutment defines the position of the test strip on the support surface. Since the test strip itself, however, is very light, a small spring force is sufficient. This spring force can, for example, be created by the test strip, upon its insertion into the strip receiver, being elastically deformed. For example, the test strip can have at least one recess near one of its edges with the contour of the strip material bordering the recess and/or the contour of an adjacent surface of the test strip receiver being so chosen that a bridge formed in the strip material by the recess is deformed upon insertion of the test strip into the strip receiver; the restoring force of the material bridge being sufficient to create the desired spring bias. For example, a nose can be formed at the boundary surface of the strip receiver which presses against the material bridge and slightly deforms it. In the reverse of this, the material bridge can also have an outwardly extending projection which projects beyond the nominal contour of the test strip edge so that the projection, and with it the material bridge, is deflected by the boundary surface of the strip receiver in the direction toward the recess. Thereby, the result again is a restoring force sufficient to press the test strip against an abutment.

The last-named embodiment allows in an advantageous way the further formation on the material bridge or on the strip receiver of a recess for partially receiving the projection. Thereby, there is achieved not only a spring force for pressing the strip against the abutment, but also a latching of the test strip to the strip receiver.

Another possibility exists in that the strip receiver has arranged in it a spring which pushes the test strip in the receiver against the abutment. The spring is, in this case, advantageously so arranged that its spring force is directed in the sense of a pushing out of the test strip from the receiver. In this case, additional advantages can be achieved if the abutment is formed on a locking element intended to be received in a recess of the test strip. On one hand, the recess can be used to quasi-code the test strip. If the recess (several recesses can also be provided in connection with several locking elements) is not entirely at the designated spot, the locking element cannot move into the recess and the spring moves the test strip again out of the measuring device as soon it is left loose. With this measuring strip, the measuring device can carry out no measurement. If further the locking element is adjustable between an inserted position and a freeing position, the spring can be used after the movement of the locking element to its freeing position to eject the test strip out of the measuring device.

According to a further feature of the invention, to solve the problem existing with of a test strip system of the initially-mentioned kind, it is proposed that the test strip receiver have at least two holding means spaced from one another at the edge areas of the support surface for holding fast the associated edges of the test strip and that the support surface, in a middle area between the holding means, be spaced vertically from these edge areas. With this arrangement, the test strip is held at its edge areas and is bent throughout its vertically-displaced middle area, and is thereby stressed so that the test field again has a definite position with respect to the support surface. For example, the support surface can be bent cylindrically, or the support surface can have a projection formed only in its middle portion which projection supports the test field so that by the bending of the test strip over the projection and the strip tension connected therewith, the test field is firmly pressed against the projection.

According to a further feature of the invention, for the solution of the mentioned object in a test strip system of the initially-mentioned type, it is proposed that the strip receiver have an outer insertion end and an inner end, that near the inner end a spring arm be arranged which rises vertically out of the support surface and toward the inner end of the strip receiver and is elastically deflectable in the direction toward the support surface, and that the spring arm have associated with it a counter-pressure surface which is spaced from the support surface and which rises away from the support surface and extends toward the inner end of the strip receiver so as to be generally parallel to the direction of the spring arm.

If a test strip is inserted into the so-formed strip receiver, it will be pressed by the spring arm against the counter-pressure surface so that it becomes bent or deflected. The restoring force created by the bending of the strip presses the free section of the strip against the support surface so that the test field again lies flatly on the support surface. In order to be able to exactly position the strip, it is advantageous if on the spring arm, a detent extension is formed for reception into a locking recess of the test strip. In contrast to the solution known from U.S. Pat. No. 5,424,035, the test strip can, despite the detention, easily be again pulled out of the device.

According to a further feature of the invention, for the solution of the above-named object in a test strip system of the initially-mentioned kind, it is proposed that above the support surface a clamping lever be pivotally supported for movement relative to the support surface about a pivot axis parallel to the support surface, which clamping lever has a clamping arm biased toward the support surface. The test strip can, therefore, be pressed against the support surface by the clamping arm. Here it also is advantageous if the clamping arm has a detent projection for reception in a detent recess of the test strip so that the test strip can be exactly positioned.

In a preferred embodiment, the clamping arm of the clamping lever is connected with a second lever arm forming an actuating arm onto which a spring engages for pushing the clamping arm against the support surface. At the same time, the clamping arm can be raised from the support surface by pressing on the actuating arm against the bias of the spring so that a test strip can fall from the strip receiver without the user having to grasp it.

To avoid a soiling of the measuring device by the test fluid dropped onto the test strip and, as the case may be, to be better able to clean the strip receiver, the strip receiver can be made as a separate element which is removably insertable in a housing of the measuring device.

According to a further feature of the invention, for the solution of the above-mentioned object in a test strip system of the initially-mentioned kind, it is proposed that the measuring device and the test strip be formed for the electrical measurement of the test field through contact elements on the measuring device and on the test strip and that at least one contact element on the measuring device is formed as a clamping spring which presses the test strip in its measuring position against the support surface. In order to release the clamping spring and to free the test strip after its use, an actuating lever is connected with the measuring device, preferably for pivotal movement about an axis parallel to the support surface, and is so associated with the at least one contact spring that the contact spring by pivoting of the actuating lever is lifted from the support surface. After the pivoting of the actuating lever, it is sufficient that the measuring device be held with the insertion opening for the test strip facing downwardly so that the used test strip can fall from the measuring device.

Further features and advantages of the invention will be apparent from the following description which in connection with the accompanying drawings explain the invention by way of exemplary embodiments.

DESCRIPTION OF THE PREFERRED EMBODIMENTS

Figure 1:
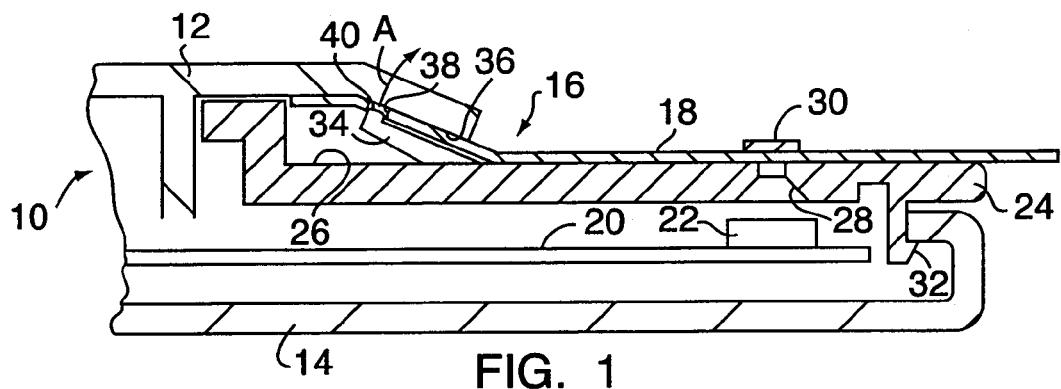
FIG. 1—a schematic partial longitudinal section through a test strip measuring device with a test strip according to a first embodiment of the invention.

The measuring system illustrated in FIG. 1 includes a measuring device 10 shown only partially in section with a housing lower portion 14 and a housing upper portion 12, as well as a strip receiver 16 in which a test strip 18 is arranged.

The measuring device is, for example, a device for the optical determination of the concentration of a given substance in a liquid, especially body liquids, for example, a device for blood sugar determination or for the quantitative determination of certain substances in urine. The housing 12,14 contains a plate 20 with a measuring optic 22 and, in addition to that, a non-illustrated electronic evaluation and control circuit. Further, the measuring device induces an operating part and an indicator device. Measuring devices of this kind are known in themselves and, therefore, do not need to be described in more detail.

The strip receiver 16 has a carrier 24 with a support surface 26 for the test strip 18, as well as a measuring opening 28 through which a test field 30 of the test strip 18 can be measured by the measuring optic 22. The carrier 24 is pushed into the housing 12,14 and held in the housing lower portion 12 by a hook 32. Provision can be made for allowing the carrier 24 to be removed from the housing 12,14 in order, for example, to clean it.

A spring arm 34 is so arranged in the carrier 24 that it rises from the support surface 26 and extends inwardly toward the inner end of the strip receiver 16. The spring arm 34 is biased in the direction of the arrow A and can be pivoted against this biasing force in the direction toward the support surface 26.

The spring arm 34 is associated with a counter-pressure surface 36 connected with the housing upper portion 12 which extends generally parallel to the spring arm 34 and is spaced a given distance from the support surface 26.

Upon insertion of the test strip 18 into the strip receiver 16, the forward end of the test strip 18, that is the end facing the inside of the device, moves between the spring arm 34 and the counter-pressure surface 36 so that the test strip 18 becomes bent. In its forward area, the test strip has a detent recess 38 into which a detent nose 40 formed on the free end of the spring arm 34 becomes inserted, if the test strip 18 is inserted fully into the strip receiver 16. In this way, the correct position of the test strip 18 in the strip receiver 16 is established, in which correct position the test field 30 is located exactly over the measuring opening 28. Because of the bending of the test strip and because of the stiffness of the strip material, a restoring force is created in the strip which presses the test field 30 firmly against the support surface 26 so that the test field 30 has a definite spacing from the measuring optic 22. As will be recognized, the test strip 18 can be inserted in simple way into the strip receiver 16 and, above all, can be again pulled out of the strip receiver in a simple way, without this simple operation encumbering the positioning accuracy.

Figure 2:
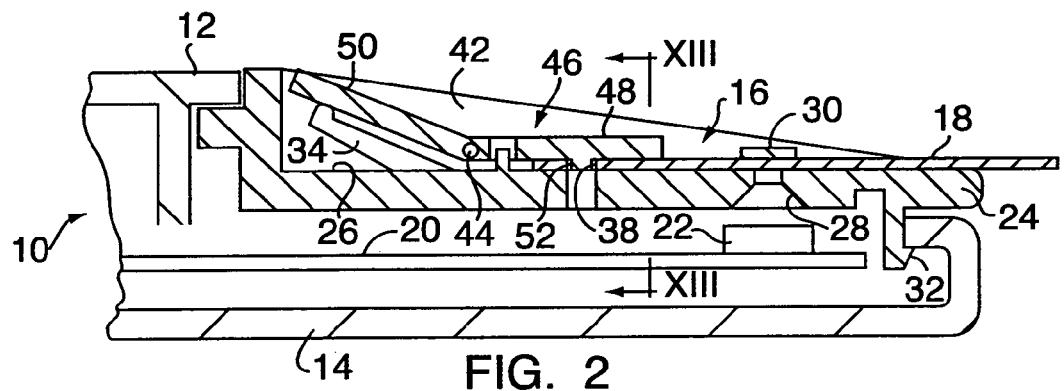
FIG. 2—a section corresponding to that of FIG. 1 through a second embodiment of the invention.
Figure 3:
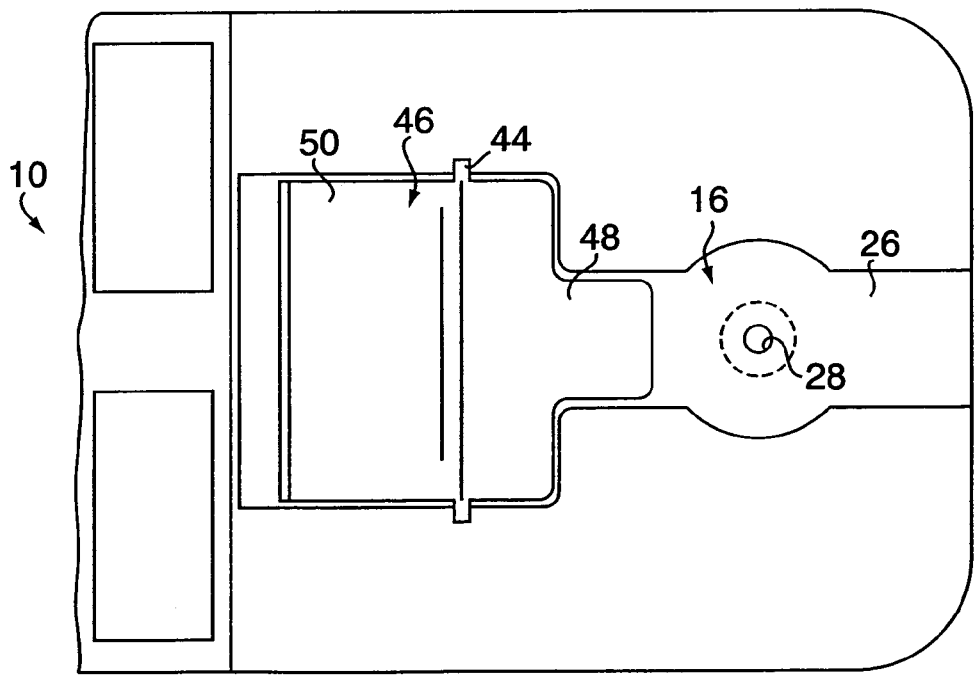
FIG. 3—a plan view of the embodiment of FIG. 2.

The solution illustrated in FIGS. 2 and 3 differ from the FIG. 1 solution in the way the test strip is held in the measuring device. The same or equivalent parts are again provided with the same reference numbers as in FIG. 1.

In the solution illustrated in FIG. 2, the counter-pressure surface 36 is omitted. In place of it, a lid-like two-armed lever 46 with a clamping arm 48 and an actuating arm 50 is pivotally supported by the side walls 42 bordering the support surface 26 of the carrier 24 for pivotal movement about a pivot axis 44. The spring arm 34 lies on the actuating arm 50 and biases the lever 46 in the clock-wise direction so that the clamping arm 48 is pressed toward the support surface 26. If, as shown in FIG. 2, a test strip 18 is inserted into the strip receiver 16, the test strip 18 at its forward section is pressed against the support surface 26 by the clamping arm 48. The position of the test strip 18 is established by a nose 52 on the lower side of the clamping arm which is receivable in a detent recess 38 of the test strip 18. In this position of the test strip 18, the test field 30 is located exactly over the measuring opening 28. This embodiment is especially simple to operate. For insertion and removal of the strip 18, the actuating arm 50 of the lever 46 is pressed downwardly; that is, the lever 46 is pivoted in the counter-clockwise direction. For removal of the test strip 18, it is sufficient, at this moment, to hold the device downwardly, so that the test strip 18 falls by itself out of the device. The operating person need not again touch the used test strip.

Figure 13:
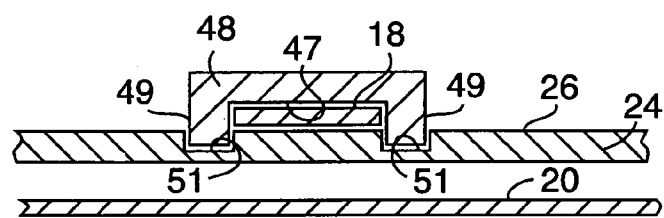
FIG. 13—a section along the line XIII-XIII in FIG. 2.

In a variant of the embodiment illustrated in FIGS. 2 and 3, the support surface 26, in which the measuring opening 28 is formed, is entirely flat and smooth. To make possible an insertion of the test strip 18, the clamping arm 48 of the clamping lever 46 has, as seen in FIG. 13, on its side facing the support surface 26 a groove shaped recess 47 in which the test strip 18 is conformably received. The edge flanges 49 of the clamping arm 48 bordering the recess 47 are received in complementary recesses of 51 in the carrier 24 to prevent a lateral shifting of the clamping arm 48 and test strip 18 and to assure a better guiding of the test strip 18.

Figure 4:
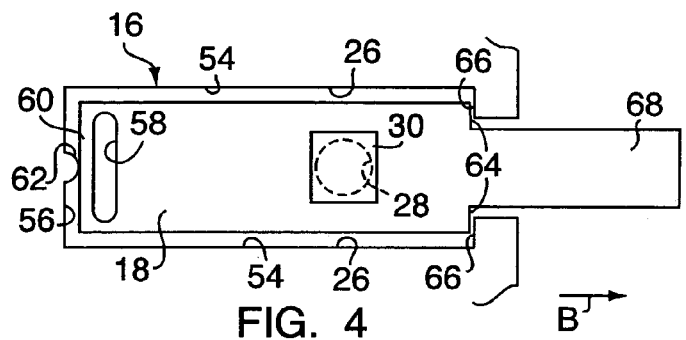
FIG. 4—a schematic plan view of a test strip receiver according to a further embodiment of the invention.

In FIG. 4 the strip receiver 16 is shown only schematically with one recognizing the support surface 26, the side wall 54 bordering the support surface 26, and the forward wall 56. In the strip receiver 16 is a test strip 18. This test strip has on its end near the forward wall 56 of the strip receiver 16 a recess 58 extending nearly over the entire strip width, so that at the forward end of the test strip 18 only a small material bridge 60 remains. At the forward wall is formed a projection 62 which presses against the material bridge 60 of the test strip and slightly deforms the bridge. By the restoring force produced in this way, the test strip is pressed rearwardly in the direction of the arrow B so that its two step surfaces 64 engage two abutment surfaces 66 formed at the insertion end of the strip receiver 16. For insertion, the test strip 18 is pushed into the strip receiver 16 so that the material bridge 60 at the forward end of the test strip is slightly deformed. Then the test strip is pressed against the support surface 26 and let loose so that its step surfaces 64 come to lie onto the abutments 66. A reverse procedure is used for removal. One grasps the test strip at its grip end 68 and lifts it slightly upwardly so that the step surfaces 64 are freed from the abutments 66. This solution also guarantees a correct positioning of the test strip on the support surface 26 so that the test field 30 comes to lie over the measuring opening 28 indicated by the dashed lines.

Figure 5:
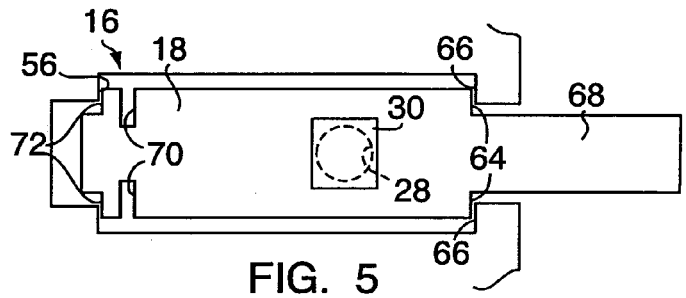
FIG. 5—a view corresponding to FIG. 4 illustrating a modified embodiment of the invention.

The embodiment, according to FIG. 5, functions according to the same principle as the embodiment of FIG. 4 with the recesses in the test strip 18 producing the spring effect being formed solely by lateral slots 70. In this case, spring tongues 72 exist at the forward end of the test strip 18 which upon their being pressed against the stepped forward wall 56 of the strip receiver 16 produce a restoring force by means of which the test strip 18 is consequently pushed to bring its step surfaces 64 against the abutments 66.

Figure 6:
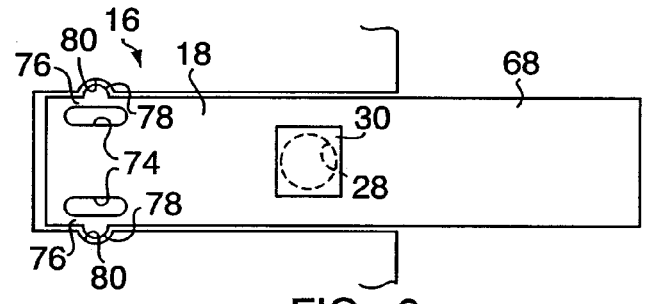
FIG. 6—a view corresponding to FIG. 4 illustrating yet another modified embodiment of the invention.

In the illustrated embodiment of FIG. 6, at the forward area of the test strip 18, near the longitudinal edges of the test strip, two slots 74 are provided which form lateral material bridges 76. These material bridges each have at their outer sides a detent nose 78 intended for reception in a complementary detent recess 80 in the side wall 54 of the test strip receiver 16. The dimensions of the noses and the width of the test strip 18 are so-chosen that the noses 78 upon insertion of the test strip 18 into the strip receiver 16 are slightly pressed together and then, upon reaching the detent recesses 80, spring outwardly. In this way, the test strip 18 is held in its measuring position.

Figure 7:
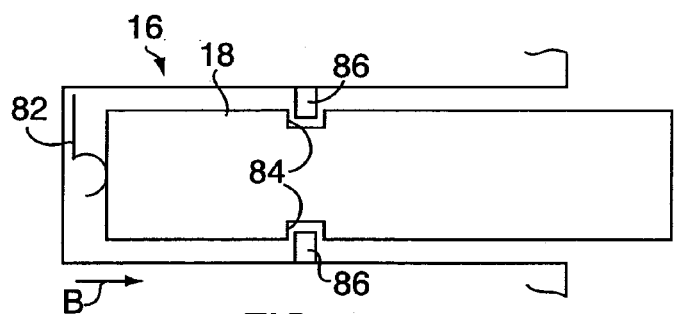
FIG. 7—a schematic plan view of a strip receiver with a spring receiver end.

In the embodiment according to FIG. 7, a spring 82 is arranged at the inner end of the strip receiver, which spring presses against the forward end of the test strip 18 and tends to push the test strip out of the strip receiver in a direction opposite to the insertion direction; that is in the direction of the arrow B. The test strip 18 has at each of its longitudinal edges a notch 84 intended for receiving an arresting element 86. The arresting element 86 is arranged in the strip receiver 16 and is movable between the arresting or receiving position illustrated in FIG. 7 and a freeing position. In the arresting position of FIG. 7, the elements 86 hold the test strip 18 firmly in the strip receiver and assure, in cooperation with the spring 82, a precise positioning of the test strip 18 inside of the strip receiver 16. When the arresting elements 86 are pressed outwardly into their freeing positions, the spring 82 pushes the test strip 18 out of the strip receiver 16, and the test strip 18 can fall out of the device without the operating person having to again touch the strip.

Figure 8:
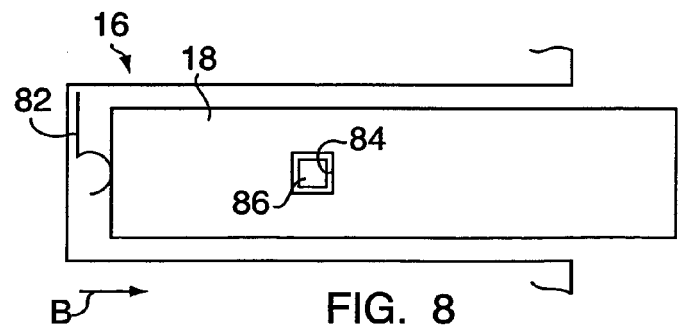
FIG. 8—a view corresponding to FIG. 7 illustrating a modified embodiment of the invention.
Figure 9:
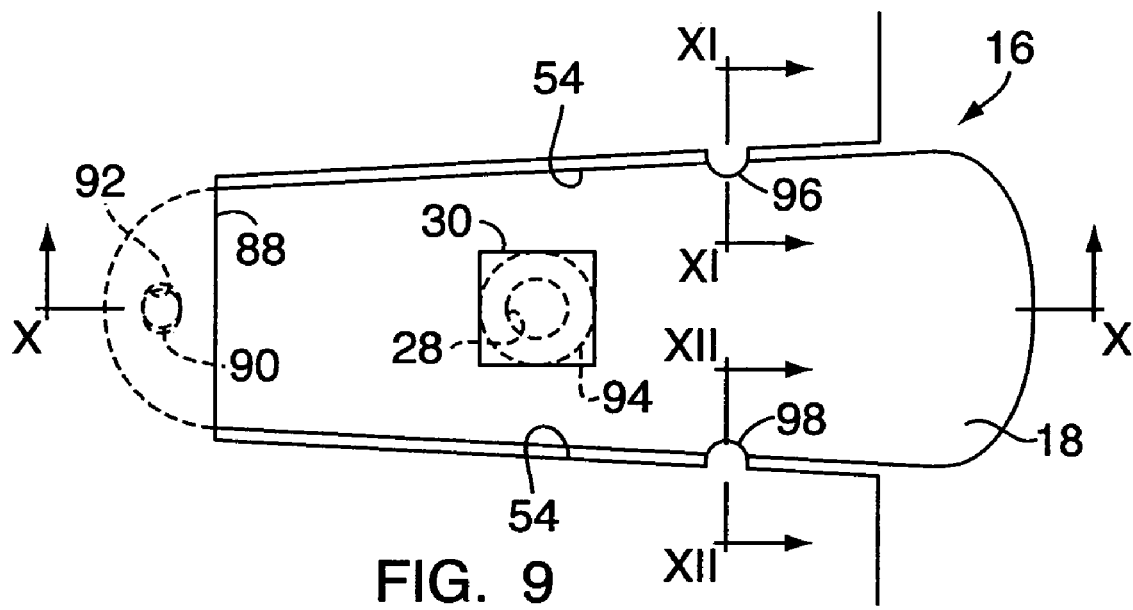
FIG. 9—a schematic plan view of a strip receiver according to a further embodiment of the invention.

The embodiment of FIG. 8 differs from that of FIG. 7 only in that, instead of two locking elements 86, a centrally-arranged locking element is provided which can be received in a corresponding central recess 84 in the test strip 18. In both embodiments, one will recognize that a test strip can only be inserted into the strip receiver 16 if it has the detent recesses or recess at a definite pre-given place. Otherwise, the spring 82 constantly pushes the test strip 18 out of the receiver. In principle, a number of locking elements can be provided at different positions in the test receiver while the test strip has only one recess corresponding to one of these locking elements, so that the test strip can be quasi-coded by the arrangement of the recess.

Figure 10:
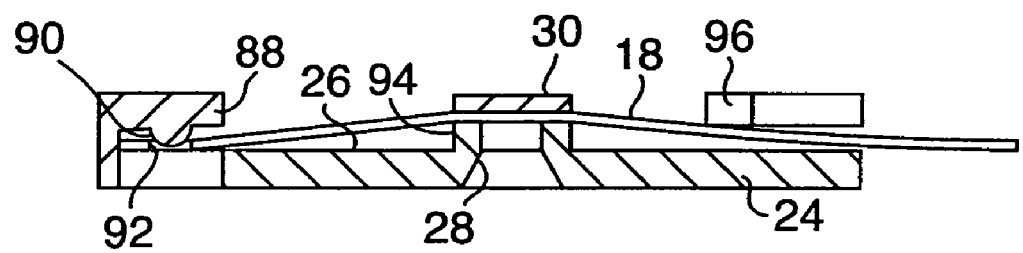
FIG. 10—a schematic longitudinal section along the line X-X in FIG. 9.

FIG. 10 shows an embodiment of the strip receiver in which the carrier 24 has a holding bar 88 at its inner end under which the forward end of the test strip 18 is insertable. A detent nose 90 is formed on the inner or underside of the holding bar 88 which nose is receivable in a corresponding detent opening 92 in the test strip 18 with which it fixes the test strip in a definite position.

Figure 11:
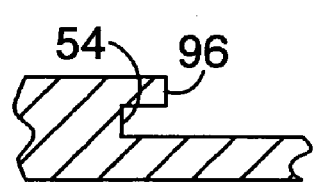
FIG. 11—a schematical section along the line XI-XI in FIG. 9.
Figure 12:
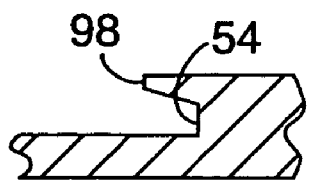
FIG. 12—a section along the line XII-XII in FIG. 9.

The measuring opening 28 is surrounded on the upper side of the support surface 26 by a ring 94 which lifts the test strip 18 slightly above the support surface 26. Near the insertion end of the strip receiver 16, two noses 96 and 98 are formed on the side walls 54 of the strip receiver 16, under which noses the associated edges of the test strip 18 can be inserted. The form of the detent noses 96 and 98 is illustrated in cross-section in FIGS. 11 and 12. Naturally, both detent noses can have the same form. As seen in FIG. 10, by the reception of the test strip under the bar 88, on one hand, and under the noses 96 and 98, on the other hand, the test strip 18 is bent over the ring 94 so that the test field 30 lies securely and flatly on the ring 94 and, therefore, has a definite spacing relative to the measuring optic lying beneath the opening 28. (Note: nose 98 is not shown in the sectional view of FIG. 10).

Figure 14:
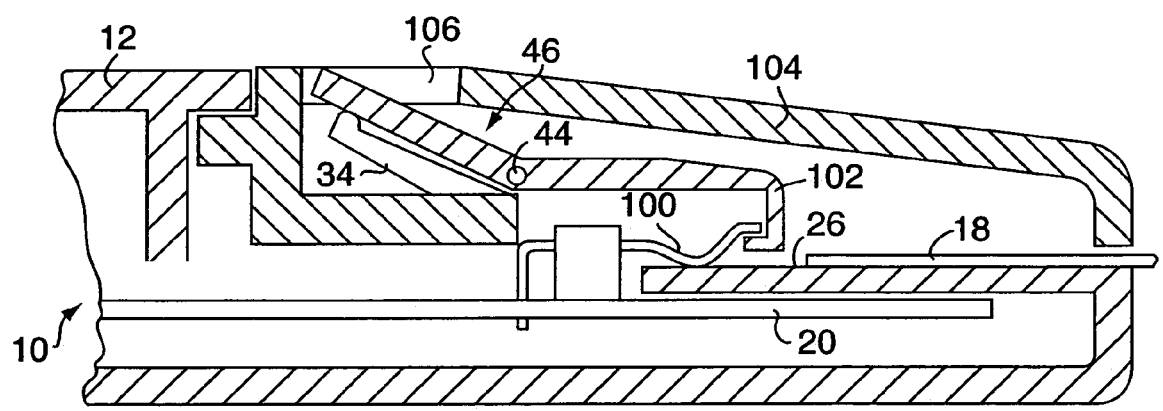
FIG. 14—a view corresponding to FIG. 2 of a further embodiment of the invention.

In the previously-described embodiments, it has always been presumed that the test field is to be measured by a measuring optic of the measuring device. FIG. 14 shows, in a schematic illustration corresponding to FIG. 2, an embodiment of the inventive measuring system by means of which the test field on the test strip 18 can be measured by way of electrical current. Similar parts are again provided with similar reference numbers.

Instead of a measuring optic, contact springs 100 are arranged on the plate 20, which, for one thing, are intended to come into contact with non-illustrated counter-contact elements on the test strip 18 when the test strip 18 is in its measuring position in the measuring device 10. For another thing, the contact springs 100 are so-formed that they urge the test strip 18 in its measuring position against the support surface 26.

The lever 46 serves in the FIG. 14 embodiment to lift the contact springs 100 from the contact elements of the test strip 18 and thereby to simultaneously free the test strip 18 so that it can fall out of the measuring device 10 when the measuring device is held with its insertion opening facing downwardly. Instead of the clamping arm 48, the lever 46 in this embodiment has a daw 102 which extends around the free ends of the contact springs 100 so that by the pivoting of the lever 46 in the counter-clockwise direction of FIG. 14, the contact springs 100 are lifted from the support surface 26 and from the test strip 18. The lever 46 can, as in the embodiment of FIGS. 2 and 3, be returned to its original position by the spring arm 34. As the case may be, the spring effect of the contact springs 100 may also be sufficient for this purpose. The measuring area of the measuring device 10, illustrated in FIG. 14, is closed by a cover 104 which has only one opening 106, through which the lever 46 can be actuated.

The invention claimed is:

1. A test field system comprising: at least one test strip with a test field, and a measuring device having a test strip receiver for measuring the test field, the test strip receiver including a support surface for the test strip and positioning means for holding the test strip inserted in the strip receiver so that at least a section of the test strip containing the test field is held in a definite position relative to the support surface, the strip receiver having two holding means spaced from one another on edge areas of the support surface for holding fast opposing ends of the test strip substantially adjacent the support surface, and a projection extending outwardly from the support surface between the two holding means and adjacent a measuring opening in the support surface the projection defining a surface vertically displaced from the support surface such that the test field of a test strip inserted in the test strip receiver is supported by the surface of the projection and spaced apart from the support surface at the measuring opening, and held substantially adjacent the support surface at the opposing ends of the test strip via the two holding means, the test strip being flexible and bent about the projection so that the test area is securely held adjacent the surface of the projection at the measuring opening.

2. A test strip system comprising: a test strip with a test field, and a measuring device for measuring the test strip, the measuring device having a test strip receiver including a support surface for the test strip and positioning means for securing the position of the test strip inserted in the strip receiver such that at least a portion of the test strip containing the test field assumes a definite position relative to the support surface, the positioning means including a pivotal two-armed lever having an actuator arm at one end thereof and a clamping arm at an opposing end, the two-armed lever supported for pivotal movement about an axis disposed parallel to the support surface and located between the actuator arm and the clamping arm, the clamping arm biased toward the support surface and engageable with a surface of the test strip opposite the support surface for securing the position of the test strip relative to the support surface, the actuator arm being operable for movement towards the support surface for insertion and removal of a test strip into the test strip receiver between the clamping arm and the support surface, the support surface for carrying the test strip during both of the insertion and testing thereof, wherein the clamping arm defines a groove in a surface thereof facing the support surface for guiding the test strip during insertion thereof in the strip receiver, and the clamping arm further comprises opposing edge flanges adjacent the groove, the edge flanges received in complementary recesses defined in the support surface when the clamping arm is in said clamping position.

3. A test strip system according to claim 2, further characterized in that the clamping arm has a detent projection for reception in a detent recess defined by the test strip.

* * * * *

UNITED STATES PATENT AND TRADEMARK OFFICE
CERTIFICATE OF CORRECTION

PATENT NO. : 7,327,451 B2 Page 1 of 1
APPLICATION NO. : 10/043681
DATED : February 5, 2008
INVENTOR(S) : Ernst Markart It is certified that error appears in the above-identified patent and that said Letters Patent is hereby corrected as shown below:

Title Page item 57, Abstract, Line 4, please delete the word "inducing" and replace with the word --including--.

Signed and Sealed this

Third Day of June, 2008

JON W. DUDAS
*Director of the United States Patent and Trademark Office*